United States Patent
Seino et al.

(10) Patent No.: US 6,194,634 B1
(45) Date of Patent: *Feb. 27, 2001

(54) APT-SENSITIVE POTASSIUM CHANNEL GENE-DEFECTIVE ANIMALS (75) Inventors: Susumu Seino; Takashi Miki, both of Chiba; Junichi Miyazaki, Suita, all of (JP)

(73) Assignees: JCR Pharmaceuticals Co., Ltd., Hyogo-ken (JP); Susumu Seino, Chiba-ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/213,864

(22) Filed: Dec. 17, 1998

(30) Foreign Application Priority Data

Jun. 10, 1998 (JP) .................................................. 10-178097

(51) Int. Cl.$^7$ ................................................. A01K 67/027
(52) U.S. Cl. ................................. 800/18; 800/8; 435/354; 435/1.1
(58) Field of Search ................................. 800/8, 9, 3, 18; 435/325, 354, 1.1

(56) References Cited

FOREIGN PATENT DOCUMENTS

| 764721 | 3/1997 | (EP) . |
| 77796/97 | 3/1997 | (JP) . |
| 97/18308 | 5/1997 | (WO) . |

OTHER PUBLICATIONS

Alcivar AA et al. Biol. Reprod. 41:1133–1142, 1989.*
Seamark RF. Progress and emerging problems in livestock transgenesis: a summary perspective. Reprod. Fertil. Dev. 6:653–657, 1994.*
Moreadith RW and Radford NB. Gene targeting in embryonic stem cells: the new physiology and metabolism. J Mol. Med. 75: 208–216, 1997.*
Mullins LJ and Mullins JJ. Transgenesis in the rat and larger mammals. J Cliln. Invest. 98:S37–S40, 1996.*
Miki T et al. Abnormalities of pancreatic islets by targeted expression of a dominant–negative K–ATP channel. Proc. Natl. Acad. Sci. 94:11969–11973, 1997.*
Milton DW. Gene targeting in the mouse. Bioessays 16:633–638, 1994.*
An English language abstract of JP 77796/97, Jun. 1997.
Ho et al., Nature, vol. 362, pp. 31–38 (1993).
Dascal et al., Proc. Natl. Acad. Sci., vol. 90, pp. 10235–10239 (1993).
Inagaki et al., J. Biol. Chem., vol. 270, No. 11, pp. 5691–5694 (1995).

Kubo et al., Nature, vol. 362, pp. 127–133 (1993).
Seikagaku, 70(2), pp. 73–83 (1998), accompanied by an English abstract.
Seino et al., Diabetes, vol. 4, No. 2, pp. 177–190 (1996).
Capecchi, Science, vol. 244, pp. 1288–1292 (1989).
Sakura et al., FEBS Letters, vol. 377, pp. 338–344 (1995).
Aguilar–Bryan et al., Science, vol. 268, pp. 423–426 (1995).
Ashcroft, Biochem. J., vol. 132, pp. 223–231 (1973).
Ashcroft, Ann. Rev. Neurosci., vol. 11, pp. 97–118 (1988).
Chandy et al., Trends Pharmacol. Sci., vol. 14, p.434 (1993).
Cook et al., Nature, vol. 311, pp. 271–273 (1984).
De Weile et al., Proc. Natl. Acad. Sci. vol. 85, pp. 1312–1316 (1988).
Henquin, Experientia, vol. 40, pp. 1043–1052 (1984).
Inagaki et al., Science, vol. 270, pp. 1166–1170 (1995).
Inagaki et al., Neuron, vol. 16, pp. 1011–1017 (1996).
Krapivinsky, Neuron, vol. 20, pp. 995–1005 (1998).
Malaisse et al., Metabolism, vol. 28, No. 4, pp. 373–386 (1979).
Noma, Nature, vol. 305, pp. 147–148 (1983).
Sturgess et al., The Lancet, vol. 8453, pp. 474–475 (1985).
Terzic et al., Am. I. Physiol., vol. 269, pp. C525–545 (1995).
Wollhein et al., Physiological Reviews, vol. 61, No. 4, pp. 914–973 (1981).
Cook et al., Diabetes, vol. 37, pp. 495–498 (1988).
Dunne et al., N. Engl. J. Med., vol. 336, pp. 703–706 (1987).
Eliasson et al., Science, vol. 271, pp. 812–815 (1996).
Gembal et al., J. Clin. Invest., vol. 91, pp. 871–880 (1993).
Kane et al, Nature Med., vol. 2, pp. 1344–1347 (1996).
Komatsu et al., Proc. Natl. Acad. Sci. USA, vol. 92, pp. 10728–10732 (1995).
Nestorowicz et al., Diabetes, vol. 46, pp. 1743–1748 (1997).
Nichols et al., Science, vol. 272, pp. 1785–1787 (1996).
Okamoto et al., Diabetes, vol. 41, pp. 1555–1561 (1992).
Pulido et al., Diabetologia, vol. 39, pp. 22–27 (1996).
Sehlin et al., Diabetes, vol. 32, pp. 820–824 (1983).
Simpson et al., Ann. Rev. Biochem. vol. 55, pp. 1059–1089 (1986).
Takasawa et al., Science, vol. 259, pp. 370–373 (1993).
Thomas et al., Science, vol. 268, pp. 426–429 (1995).
Thomas et al., Cell, vol. 44 pp. 419–428 (1986).
Wang et al., J. Clin. Invest., vol. 84, pp. 62–67 (1989).
Wollheim et al., Method of Enzymology, eds. Fleisher et al., (Academic Press Inc., San Diego), CO1. 192, pp. 188–223 (1990).

(List continued on next page.)

*Primary Examiner*—Bruce R. Campell
*Assistant Examiner*—Ram Shukla
(74) *Attorney, Agent, or Firm*—Greenblum & Bernstein, P.L.C.

(57) ABSTRACT

A Kir6.2 gene-defective, non-human mammal, a mouse in particular, its tissues and cells are provided, wherein the ATP-sensitive potassium channel Kir6.2 gene, one of the subunits of $K_{ATP}$ channels essential for insulin secretion by pancreatic β-cells, is lost from one or both of the allelic loci.

3 Claims, 10 Drawing Sheets

OTHER PUBLICATIONS

Thomas et al., "Mutation of the Pancreatic Islet Inward Rectifier Kir6.2 also Leads to Familial Persistent Hyperinsulinemic Hypoglycemia of Infancy", *Human Molecular Genetics*, vol. 5, No. 11, pp. 1809–1812 (1996).

Miki et al., "Defective Insulin Secretion and Enhanced Insulin Action in $K_{ATP}$ Channel–Deficient Mice", *Proc. Natl. Acad. Sci.*, vol. 95, pp. 10402–10406 (1998).

Sakamoto et al., "Pathophysiological Role of Sarcolemmal ATP–Sensitive $K^+$ Channel: Electrophysiological Analysis Using Kir6.2 Knockout Mice", *Japanese Journal of Pharmacology*, vol. 79, No. Supp. 1, p. 104p. 1999.

Miki et al., "The Structure and Function of the ATP–Sensitive $K^+$ Channel in Insulin–Secreting Pancreatic β–cells", *Journal of Molecular Endocrinology*, 22, pp. 113–123 (1999).

* cited by examiner

APT-SENSITIVE POTASSIUM CHANNEL GENE-DEFECTIVE ANIMALS

FIELD OF THE INVENTION

The present invention relates to gene-defective (knockout) animals and in particular to gene-defective mice, and above all to ATP-sensitive potassium channel gene-defective mice.

BACKGROUND OF THE INVENTION

Insulin, which is secreted by pancreatic β-cells, is a hormone that lowers blood glucose levels, and glucose is one of the important physiological stimulants of its secretion. The mechanisms of glucose-induced insulin secretion have been studied vigorously, primarily based on the glucose metabolism hypothesis, for over the last two decades, [Malaisse W. J., et al., Metabolism, 28:373–386 (1979)]. The hypothesis, which has widely attracted attention, has been placing emphasis on the probability of glucose metabolites in pancreatic β-cells acting as signals for insulin secretion. Among a variety of metabolites, ATP has been thought to be one of the most important molecules, functioning, as a metabolic energy carrier, as the intracellular signal for insulin secretion in pancreatic β-cells [Ashcroft, S. J. H., Biochem. J., 132:223–231 (1973)].

Pancreatic β-cells are electrophysiologically excitable cells, and it was known that the membrane potential of β-cells is the key factor in the stimulus-secretion coupling in insulin release [Henquin J. C., Experimentia 40:1043–1052 (1984)]. It was also known that glucose regulates β-cell membrane potential by controlling the permeability of the membrane to potassium ion [Sehlin, J., Diabetes, 32:820–323 (1983)].

Then, in 1984, after Cook et al. discovered ATP-sensitive potassium channels ($K_{ATP}$), a molecule was first revealed that links glucose metabolism with potassium permeability of the membrane [Cook, D. L. et al., Nature, 311:271–273 (1984)]. $K_{ATP}$ channels, originally discovered in cardiac muscle, were characterized by inhibition of the channels when intracellular ATP concentration is increased [Noma, A., Nature, 305:147–148 (1983)]. Subsequently, $K_{ATP}$ channels were found in a variety of tissues and cells, including the brain, pituitary gland and skeletal muscles [Ashcroft, FM, Annu. Rev. Neurosci., 11:97–118 (1988)].

According to the insulin secretion mechanism of pancreatic β-cells, ATP produced by glucose metabolism causes closure of the $K_{ATP}$ channels, which in turn leads to depolarization of the β-cell membrane, which is followed by opening of the voltage-dependent calcium channels, thereby allowing $Ca^{2+}$ influx into the β-cells. The thus resulted rise of intracellular $Ca^{2+}$ concentration triggers $Ca^{2+}$-dependent insulin secretion [Wollheim, C. B. et al., Physiol. Rev., 61:914–973 (1981)]. Thus, the $K_{ATP}$ channels of the β-cells, which link the metabolic status of the cell to its membrane potential, are key molecules, and they are thought to act as intracellular ATP- and ADP-sensors, thereby regulating the excitability of the membrane.

Sulfonylureas (Su agents), insulin secretagogue oral hypoglycemic agents which are widely used threapeutics in the treatment of non-insulin dependent diabetes mellitus (NIDDM), were shown to inhibit the activity of $K_{ATP}$ channels of β-cells [Sturges, N. C. et al., Lancet, 8453:474–475 (1985), De Weille, J., Proc. Natl. Acad. Sci. USA, 85:1312–1316 (1988)]. Electrophysiological studies on $K_{ATP}$ channels have shown that their kinetics and pharmacological properties vary among tissues, suggesting that $K_{ATP}$ differs among tissues structurally and functionally [Terzic, A. et al., Am. I. Physiol., 269:C525–C545 (1995)]. Since $K_{ATP}$ channels in pancreatic β-cells and insulin-secreting cell lines have the property of inward rectification, they could be structurally related to other channels that constitute the inwardly rectifying $K^+$ channel family. Inwardly rectifying $K^+$ channels are distinguished from voltage-gated $K^+$ channels (Kv) in that the former are not activated by membrane depolarization and they allow greater $K^+$ influx than efflux.

In understanding the structure and function of the inwardly rectifying $K^+$ channels, a breakthrough was brought about by expression cloning of cDNAs encoding three distinct inwardly rectifying $K^+$ channels: ROMK1 (Kir 1.1) from rat kidney [Ho, K. et al., Nature, 362:31–38 (1993)], IRK1 (Kir 2.1) from a mouse macrophage cell line [Kubo, Y. et al., Nature, 362:127–133 (1993)], and KGA (Kir 3.1) from rat heart [Dascal, N. et al., Proc. Natl. Acad. Sci. USA, 90:10235–10239 (1993)]. These studies have established new Kir family genes encoding proteins with different structural and functional characteristics from those of Kv super family. Today, subfamilies of Kir are designated Kir 1.0–7.0 according to the nomenclature of Chandy and Gutman [Chandy, K. G., Gutman, G. A., Trends Pharmacol. Sci., 14:434 (1993). Krapivinsky, G. et al., Neuron 20, 995–1005(1998)].

Using a GIRK1 cDNA as a probe, a new member of the Kir family, $uK_{ATP}$-1 (Kir 6.1), has been isolated from a variety of tissues [Inagaki, N., J. Biol. Chem., 270:5691–5694 (1995)]. And, a novel Kir gene, human Kir6.2 (referred also to as "BIR"), has been isolated by screening a human genomic library using a Kir 6.1 cDNA as a probe, and, further, mouse Kir6.2 (mBIR) gene has been obtained by screening $7 \times 10^5$ plaques from a mouse insulin secreting cell line MIN6 cDNA library under standard hybridization conditions, the DNA sequences of which, for human and mouse, respectively, have been disclosed (Japanese Unexamined Patent Publication 77796/97). The DNA sequence of mouse Kir6.2 gene is set forth in Sequence Listing (SEQ ID No:1).

The Kir6.2 is made up of 390 amino acid residues and there is observed 96% identity between human Kir6.2 and mouse Kir6.2. Further, sulfonylurea receptor (SUR) has been found by Aguilar-Bryan et al. in the process of cloning Kir6.2 (BIR) [Aguilar-Bryan, L. et al., Science, 268:423–426 (1995)]. Now it is known that the pancreatic β-cell $K_{ATP}$ channel comprises at least two subunits, a Kir6.2 (BIR) and a sulfonylurea receptor (SUR), and mutation occurred in the $K_{ATP}$ channel gene is considered to be one of the main causal factors of non-insulin dependent diabetes mellitus. For the diversity and functions of inward-rectifying potassium channels, see Horio, Y., SEIKAGAKU, 70(2), p.73–83 (1998), and Seino, S. et al., DIABETES REVIEWS,4(2),177–190 (1996).

Today, diabetes mellitus is a disease of a national scale, the number of its patients including potential ones reaching several million in Japan and the United States, and 5–10% of the middle aged or over are estimated to be diabetic patients. Diabetes mellitus is classified into type I (IDDM), which is insulin-dependent, and type II (NIDDM), non-insulin dependent, and the non-insulin dependent type II constitutes more than 90% of the number of the diabetic patients. As aforementioned, the relation between non-insulin dependent diabetes mellitus and ATP-sensitive potassium channels is being gradually elucidated. However, development of new therapeutics for NIDDM has been retarded, for such experimental animals have not been obtained that are necessary for enabling studies on the physiological role of the ATP-sensitive potassium channel and for enabling thereupon development of improved therapeutics for non-insulin dependent diabetes mellitus.

On the other hand, creation of model animals which have mutation in a particular gene is an important means in studying the functions of the gene which causes various pathological states, and leading to development of diagnostic drugs or therapeutics or methods of treatment. Recent advancement in molecular biology has established techniques to introduce deletion or mutation into a desired gene on the mouse chromosomes by means of gene-targeting in mouse embryonic stem cells (ES cells), thereby enabling to produce knockout mice, i.e. a mouse in which a particular gene is destroyed [Capecchi, M. R., Science, 244:1288–1292 (1989)].

The $K_{ATP}$ channel in pancreatic β-cells comprises subunits, a sulfonylurea receptor (SUR1) and a Kir6.2 [Inagaki, N. et al., Science, 270:1166–1170 (1995), Sakura, H. et al., FEBS Lett., 377:338–344 (1995)], whereas the $K_{ATP}$ channel in skeletal muscle or cardiac muscle comprises a SUR2A and a Kir6.2 [Inagaki, N. et al., Neuron, 16:1011–1017 (1996)]. As it is thought to be the Kir6.2 that serves to form a $K^+$ selective pore of the $K_{ATP}$ channel, we assumed that mice devoid of $K_{ATP}$ channels could be created by disrupting Kir6.2 gene. Based upon this assumption, the objective of the present invention is to produce gene-defective (knockout) animals, especially gene-knockout mice, in which Kir6.2 gene, the gene of one of the subunits of $K_{ATP}$ channels, is lost. Such animals are necessary for elucidating the function and physiological role of $K_{ATP}$ channels, the essential molecules in insulin secretion by pancreatic β-cells, and for development of therapeutics for non-insulin dependent diabetes mellitus.

SUMMARY OF THE INVENTION

Thus, the present invention provides a Kir6.2 gene-defective, homozygotic non-human mammal, wherein the ATP-sensitive potassium channel Kir6.2 gene is lost from both of the allelic loci. The non-human mammal preferably is a mouse.

Moreover, the present invention also provides a Kir6.2 gene-defective, heterozygotic non-human mammal, wherein the ATP-sensitive potassium channel Kir6.2 gene is lost from only one of the both allelic loci. The non-human mammal preferably is a mouse.

In addition, the present invention also provides tissues of those non-human mammals. The term "tissues" includes pancreatic tissue, and tissues of cardiac muscle, skeletal muscle, brain, vascular endothelium, and any other tissues.

Still further, the present invention provides cells of those non-human mammals. The term "cells" includes Langerhans' β-cells, skeletal muscular cells, myocardial cells, pituitary gland cells and vascular endothelial cells and any other cells.

By providing animals, tissues and cells devoid of certain ATP-sensitive potassium channel Kir6.2 gene which relates directly to the onset of non-insulin dependent diabetes mellitus (NDDM), the present invention will help studies of etiological mechanisms of NDDM and accelerate development of improved therapeutics for NDDM.

DETAILED DESCRIPTION OF THE INVENTION

The development of techniques to culture mouse ES cells while maintaining its totipotency, and vector systems that effect homologous recombination in cultured cells [Thomas, K. T. and Capecchi, M. R., Cell, 44:419–428 (1986)] have made it possible to carry out gene-targeting on Kir6.2 gene. That is, by isolating Kir6.2 gene from a mouse genomic library using a DNA probe, destroying the gene by inserting therein a selectable marker gene, introducing vectors incorporated with the destroyed gene into cultured ES cells thereby allowing homologous recombination to occur, isolating and identifying a clone in which homologous recombination has been effected, injecting the clone into a blastocyst, thus a chimeric mouse can be obtained. As the injected ES cells retain ability to differentiate into germ cells and therefore the genetic information from the mutant ES cells will be transferred at certain probability to its progeny, crossing between F1 animals can produce Kir6.2 gene-defective homozygotic (Kir6.2$^{-/-}$) mouse in which Kir6.2 gene is lost from both of the allelic loci. Determination of whether the mouse is of Kir6.2$^{-/-}$ is made by extracting genomic DNA from the tail of the mouse, digesting it with EcoRI and BglII, and then Southern blotting using a probe of about 0.6 kb Kir6.2 gene fragment located about 4 kb downstream of the XhoI site in Kir6.2 gene, which fragment is not included in the targeting vector. Once Kir6.2$^{-/-}$) mice has been obtained, their crossing will make it possible to maintain mice with that characteristic, and, moreover, Kir6.2 gene-defective, heterozygotic (Kir6.2$^{+/-}$) mice will be readily obtained in which Kir6.2 gene is lost from only one of the both allelic loci, by crossing a Kir6.2$^{-/-}$ mouse with a normal (Kir6.2$^{+/+}$) mouse. The same method is also be applicable to other animal species.

The present invention will be described in further detail with reference to an example. It however is not intended that the present invention be restricted to the example.

EXAMPLE

<Kir6.2 Gene Targeting>

Figure 1:
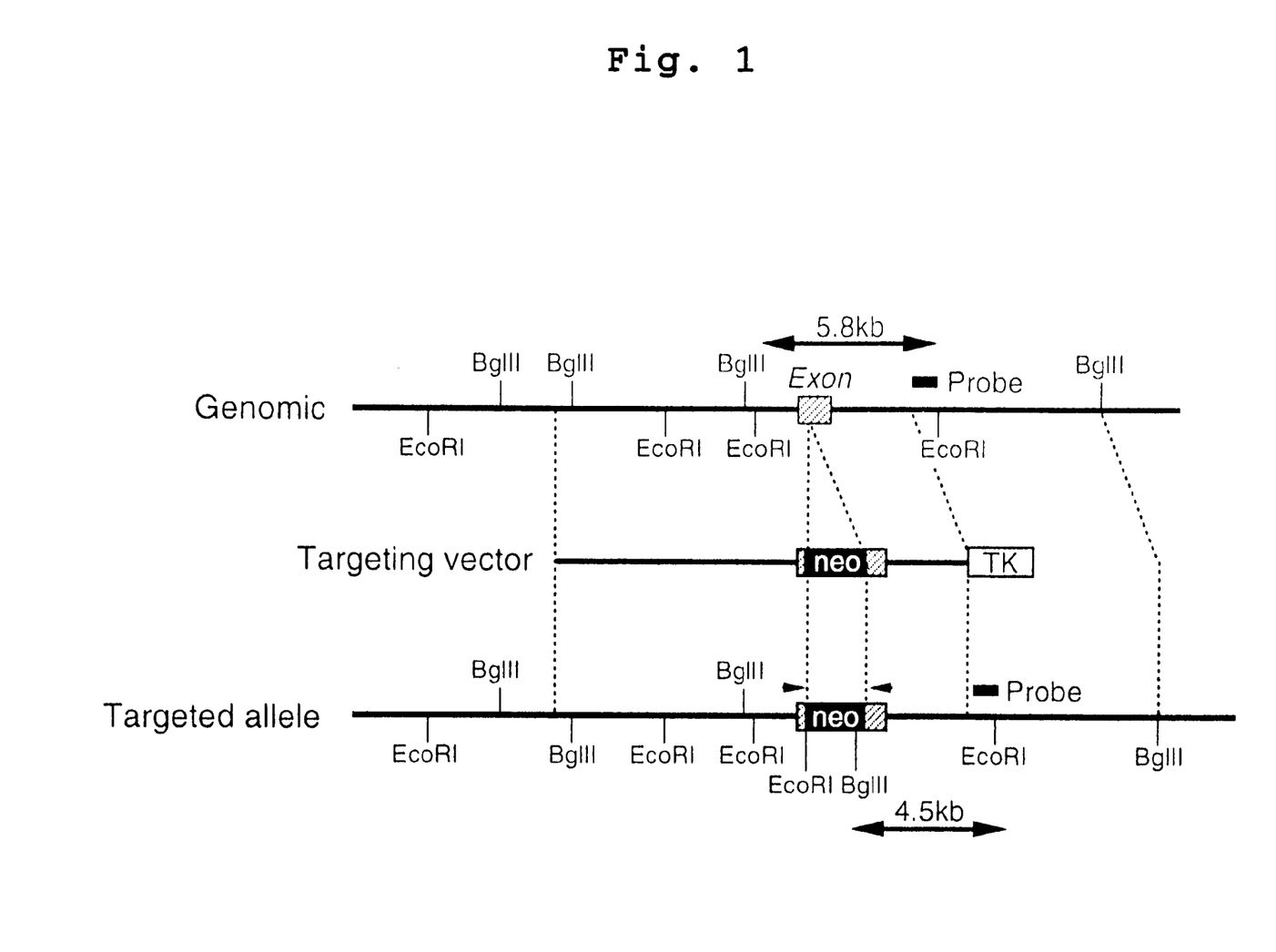
FIG. 1 illustrates the scheme showing mouse Kir6.2 gene, a targeting vector to be used, and the homologous recombination conjugate.

Referring now to FIG. 1, a scheme is given showing part of genomic DNA including mouse Kir6.2 gene (SEQ ID NO: 1), a targeting vector to be used, and the targeted allele, i.e. homologous recombination conjugate. In the figure, the exon is indicated by hatched boxes. It is known that Kir6.2 gene contains no intron. Neo and TK represent a neomycin-resistant gene and a thymidine kinase gene, respectively. "Probe" indicates the probe site for Southern blotting analysis, and the arrow heads represent the primers for RT-PCR. As shown in the figure, the neomycin-resistant gene "neo", a marker for positive selection, was inserted into the targeting vector, utilizing the restriction enzyme XhoI site within Kir6.2 gene. Outside the homologous region, a restriction enzyme XhoI site was inserted. The procedure for preparing a gene-targeting vector is as follows.

The $K_{ATP}$ channel Kir6.2 gene was isolated from a 129/Sv mouse genomic library Lambda FIXII (Stratagen) with the aid of a cDNA probe. The probe used was a DNA fragment of about 1.2 kb cut out, with SmaI and PmaCI, from the cDNA plasmid including mouse Kir6.2 we had cloned (Science, 17: 1166–1170, 1995). The DNA fragment includes the sequence from the SmaI site at 5'UT to the PmacI site at 3'UT of Kir6.2. The probe was labeled with radioisotope $^{32}P$ utilizing nick-translation, and used to screen the genomic DNA library under high stringent conditions, thus isolating nine positive clones. As two clones found identical ones in the rest of clones, restriction maps were produced for the seven positive clones. The restriction maps were produced with SacI, BamHI, BglII, SphI, EcoRI, ScaI, XbaI, NheI, DraI, XhoI, SmaI, and NotI.

The Kir6.2 gene targeting vector was prepared as follows: A part was chosen as a homologous region for the targeting vector, between the site by 8.0 kb in the 5'-direction and the site by 3.8 kb in the 3'-direction, both from the XhoI site within the amino acid encoding region of Kir6.2 gene. A neomycin-resistant gene "neo", a positive selection marker, was inserted into the XhoI site, and a herpes simplex virus thymidine kinase gene, a negative selection marker, was inserted downstream of the 3'-end of the homologous region. The targeting vector was prepared using pBluescript II KS+ (Stratagene). As it has a NotI site upstream of the 5'-end of the homologous region, it can be linearized by digestion with NotI.

<Preparation of ES Cells (Embryonic Stem Cells)>

For ES cells, E14 cell line was used which had been established from 129/01a, and was a gift from Professor S. Aizawa of Kumamoto University. The ES cells were stored in liquid nitrogen and cultured before use in a 15% FCS-DMEM containing LIF, NEAA and pyruvic acid.

<Preparation of Feeder Cells>

Feeder cells were prepared from transgenic mice expressing neo, the neomycin-resistant gene. 14.5-day old fetus of neomycin-resistant gene transgenic mice was removed of extraembryonic tissues and viscera, then minced and dispersed by rocking for 50 min at 37° C. in a 0.1% trypsin solution prepared by 25 fold dilution of GIBCO-BRL 2.5% trypsin with 5.9 mM EDTA-PBS. The cells were suspended in 10% FCS-DMEM high glucose, centrifuged once and cultured in 10-cm dishes in 10% FCS-DMEM high glucose to give the first generation culture. Feeder cells were cultured for two hours in 10% FCS-DMEM high glucose containing 10 μg/ml mitomycin the previous day before use and subcultured, and used as feeder cells on the following day.

<Incorporation of the Gene into the ES Cells>

Incorporation of the gene into the ES cells was carried out by electroporation using Gene pulser II (BioRad). 120 μg of the targeting vector was digested with NotI, treated once with phenol/chloroform and then once with chloroform, precipitated with ethanol, and adjusted to 300 μg/ml with PBS. Prior to electroporation, the ES cells were scraped off and suspended in PBS at 1.43×10⁷ cells/ml. Four cuvettes were prepared each containing 0.7 ml of this ES cell suspension (10⁷ cells/cuvette) and 0.1 ml of the targeting vector DNA (total 4×10⁷ cells), pipetted, allowed to stand on ice for 10 minutes, and subjected to pulses at 210V, 500 μF.

<Selection of Colonies>

After electroporation, the cells in one of the cuvettes were transferred into a Falcon 2058 tube and suspended by addition of 1 ml of the medium. The cells were dispersed by further addition of 38 ml of the medium and plated by 10 ml each on four 10-ml dishes that had been plated with feeder cells. 36 hours after electroporation, selection was started with 250 μg/ml G418 (neomycin, geneticin: Gibco BRL), and after 48 hours with 250 μg/ml G418 and 0.2 nM FIAU (1-[2-deoxy-2-fluoro-β-D-arabinofranosyl]-5-iodouracyl).

<Harvesting of Colonies>

Colonies were harvested on the eighth day from the electroporation. The colonies were sucked into 96-well dishes containing 10 μl of 0.25% trypsin EDTA, incubated for 6 minutes at 37° C. 50 μl PBS was added, and the cells were dispersed by pipetting and plated by 30μl each on two 96-well dishes with plated feeder cells. One of the dishes was put in freeze storage for blastocyst injection, and the other was cultured for extraction of genomic DNA for screening.

<Identification of Clones with Effected Homologous Recombination>

DNA was collected from the harvested neomycin-resistant ES cells through phenol/chloroform extraction, chloroform extraction, then precipitation with ethanol, and washing with 70% ethanol. Those with effected homologous recombination were selected by digesting 10 μg of thus collected genomic DNA with EcoRI and BglII, and Southern blotting using a probe of about 0.6 kb Kir6.2 gene fragment located about 4 kb downstream of the XhoI site in the KirG.2 gene, the fragment not included in the targeting vector. 393 ES cells were screened and one clone with effected homologous recombination was identified.

<Creation of Kir6.2 gene-defective homozygotic mice>

3.5-day old undifferentiated embryos were taken from pregnant 129/SV mice and underwent microinjection with about 20 of the subcultured mutant ES cells, then transplanted into the uterus of surrogate mothers, giving chimeric mice through natural delivery.

Figure 2:
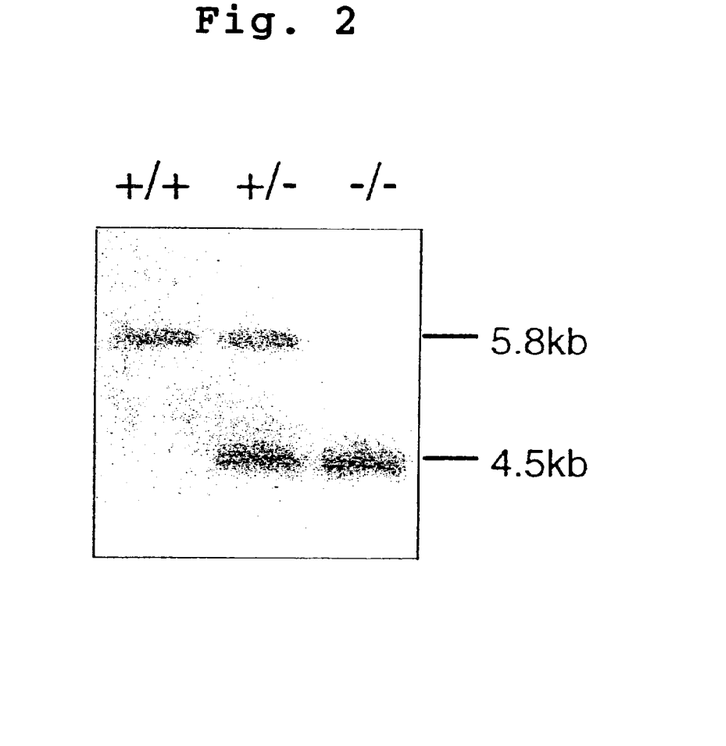
FIG. 2 illustrates the result of Southern blotting analysis on the second generation.

Then, males of these chimeric mice were crossed with wild-type females to obtain the second generation (F1) mice, which were then crossed each other to obtain the third generation (F2) mice. Some of the third generation (F2) mice were Kir6.2 gene-defective homozygotic (Kir6.2$^{-/-}$) mice obtained by crossing between heterozygotic (Kir6.2$^{+/-}$) mice (which were devoid of the Kir6.2 gene in only one of the both allelic loci), and they were selected to give the Kir6.2 gene-defective, homozygotic (Kir6.2$^{-/-}$) mice of the present invention. FIG. 2 illustrates the Southern blotting analysis. In the figure, the lane +/+ indicates wild-type, +/− heterozygote, −/− Kir6.2 gene-defective homozygote. Southern blotting analysis was carried out by digesting 10 μg of the extracted genomic DNA with EcoRI, BglII, and probing with a Kir6.2 gene fragment of about 0.6 kb located about 4 kb downstream of the XhoI site in the Kir6.2 gene, the fragment not included in the targeting vector.

Tissues were sampled from the pancreas, heart and brain of the Kir6.2 gene-defective homozygotic mice and control mice, and RNAs were prepared by GTC method. Based upon the RNAs, single stranded DNAs were prepared using random hexamers as primers. Using them as templates, PCR (RT-PCR) was carried out with the aid of primers selected within the Kir6.2 gene, confirming that Kir6.2 gene has not been transcribed in the Kir6.2 gene-defective homozygotic mice.

Figure 3:
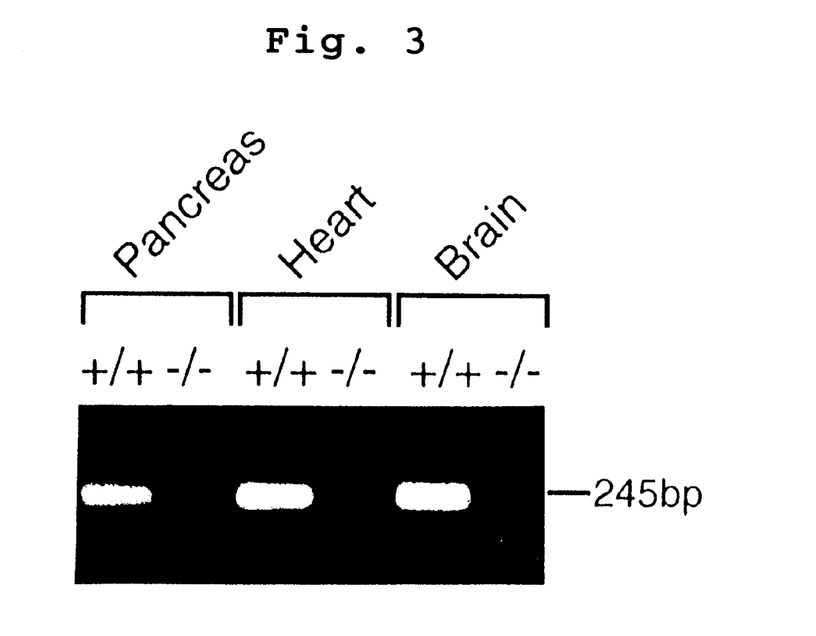
FIG. 3 illustrates the results of the RT-PCR analysis with the pancreas, heart and brain of Kir6.2$^{+/+}$ and Kir6.2$^{-/-}$ mice.

FIG. 3 illustrates the results of the RT-PCR analysis with the pancreas, heart and brain of Kir6.2$^{+/+}$ and Kir6.2$^{-/-}$ mice, respectively. Total 10 μg of RNA was extracted from each of the tissues to prepare cDNA. Kir6.2 transcription products were found in Kir6.2$^{+/+}$-type tissues but not in Kir6.2 $^{-/-}$-type tissues. The expected length of the product by the Kir6.2 RT-PCR was 245 base pairs.

The Kir6.2 mice grew as normal, having reproducibility, and there were no apparent abnormalities in their general appearance or behavior. The Kir6.2$^{-/-}$ mice thus obtained can be maintained through their mutual crossing. In addition, Kir6.2 gene-defective heterozygotic (Kir6.2 $^{+/-}$) mice can be produced by crossing between Kir6.2$^{-/-}$ mice and Kir6.2 $^{+/+}$ mice.

[Detection and Function Analysis of $K_{ATP}$ Channel]
<Electrophysiology and Determination of Intra-cellular Calcium Concentration>

To confirm the absence of functionable $K_{ATP}$ channels in Kir6.2 gene-defective homozygotic mice, we examined the whole cell membrane currents, single channel currents and intracellular calcium concentration in normal (Kir6.2$^{+/+}$) pancreatic β-cells and Kir6.2$^{-/-}$ cells.

Pancreatic islets were isolated by collagenase digestion method [Wollheim, C, et al., in Methods in Enzymology, eds. Fleischer, S. & Fleischer B., (Academic Press Inc., San Diego), vol.192, p.188–223 (1990)], and dispersed islet cells were cultured in DMEM supplemented with 10% FCS, then plated onto 3.5-cm dishes containing CELLocate Coverslips (Eppendorf, Hamburg, Germany), and incubated at 37° C. for 24–72 hours before experiments.

The whole-cell recordings, single channel recordings, and measurements of intracellular calcium concentration in a single pancreatic β-cell were performed as previously described [Miki T. et al., Proc. Natl. Acad. Sci. USA. 94, 11969–11973 (1997)]

Figure 4:
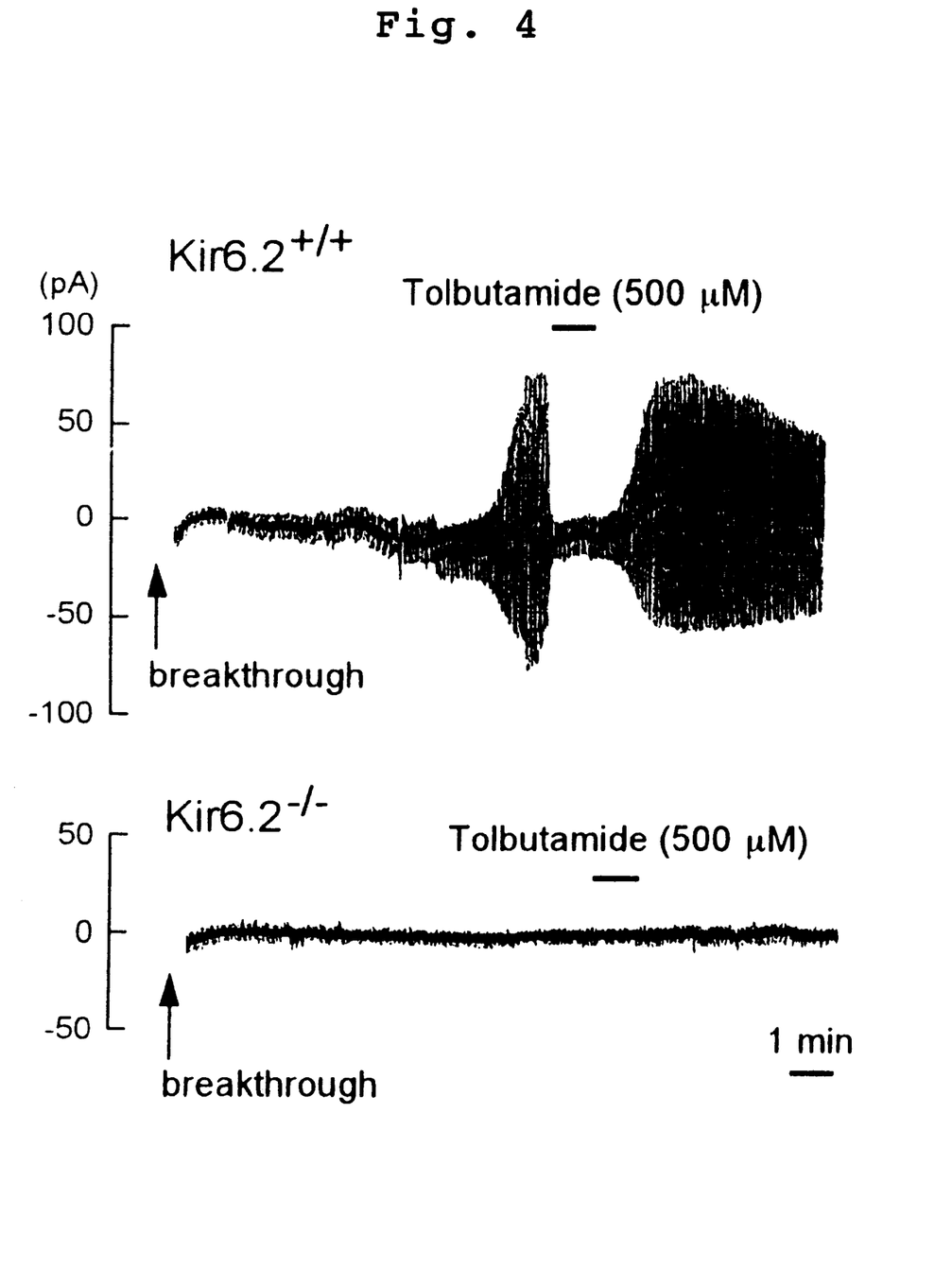
FIG. 4 is a graph showing whole-cell membrane currents in pancreatic β-cells.

Referring to FIG. 4, under the holding potential of −70 mV, alternate voltage pulses of ±10 mV and 200 msec duration were applied every 2 sec to the pancreatic β-cells. Dialysis of the Kir6.2$^{+/+}$ pancreatic β-cells intracellularly with a ATP-free pipette solution (breakthrough) caused progressive increase in K$^+$ conductance of the membrane. This increase was promptly inhibited by 500 μM tolbutamide, which property is characteristic of the $K_{ATP}$ channels in pancreatic β-cells. In contrast, no increase was observed in K$^+$ conductance in Kir6.2$^{-/-}$ pancreatic β-cells after dialysis or tolbutamide treatment.

Figure 5:
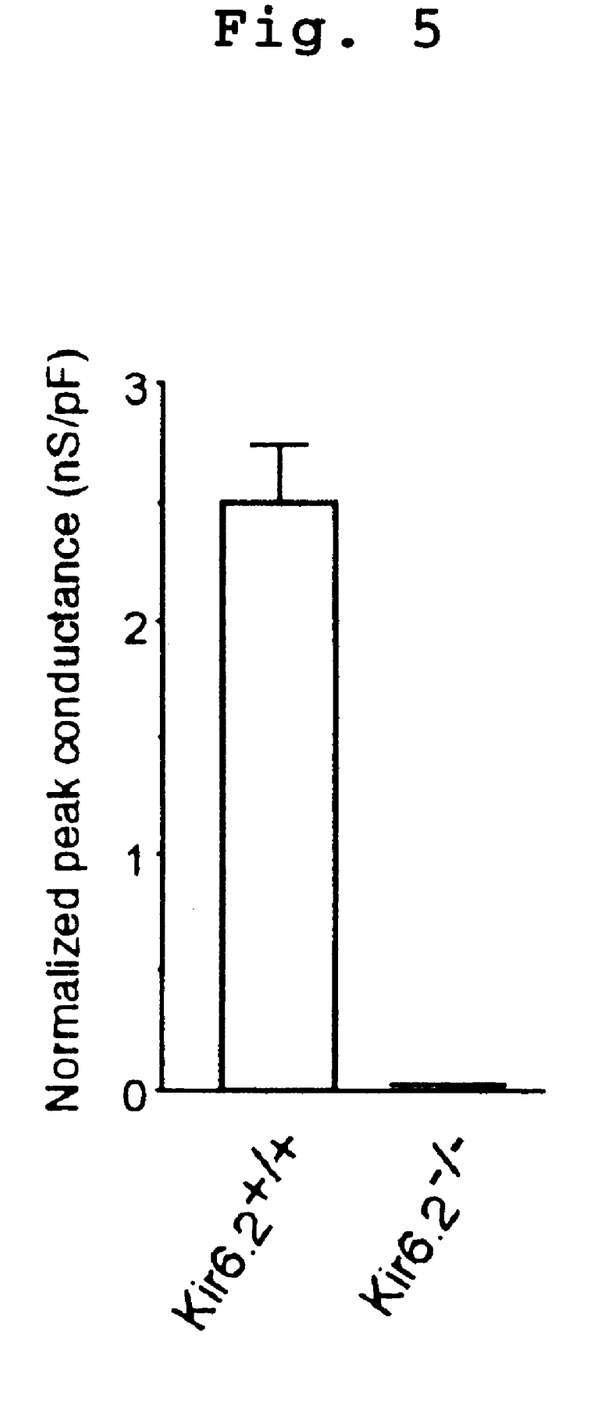
FIG. 5 is a graph showing $K_{ATP}$ channel conductance of pancreatic β-cells.

Complete loss of $K_{ATP}$ channel activity in Kir6.2$^{-/-}$ pancreatic β-cells was further confirmed by single channel analysis. Unitary $K_{ATP}$ channel currents were detected in 39 patches out of 40 (39/40=97.5%) in Kir6.2$^{+/+}$ pancreatic β-cells, whereas no currents were detected in Kir6.2$^{-/-}$ pancreatic β-cells (0/40=0%). The absence of $K_{ATP}$ channel activity in Kir6.2$^{-/-}$ mice was also confirmed in skeletal muscle. These results indicates that the Kir6.2 expression protein is an essential subunit for $K_{ATP}$ channel functions. FIG. 5 illustrates the $K_{ATP}$ channel conductance of pancreatic β-cells. To eliminate the influence of differing membrane areas among cells, recorded ATP-sensitive conductance was normalized by dividing that by the membrane capacitance for each cell.

Figure 6:
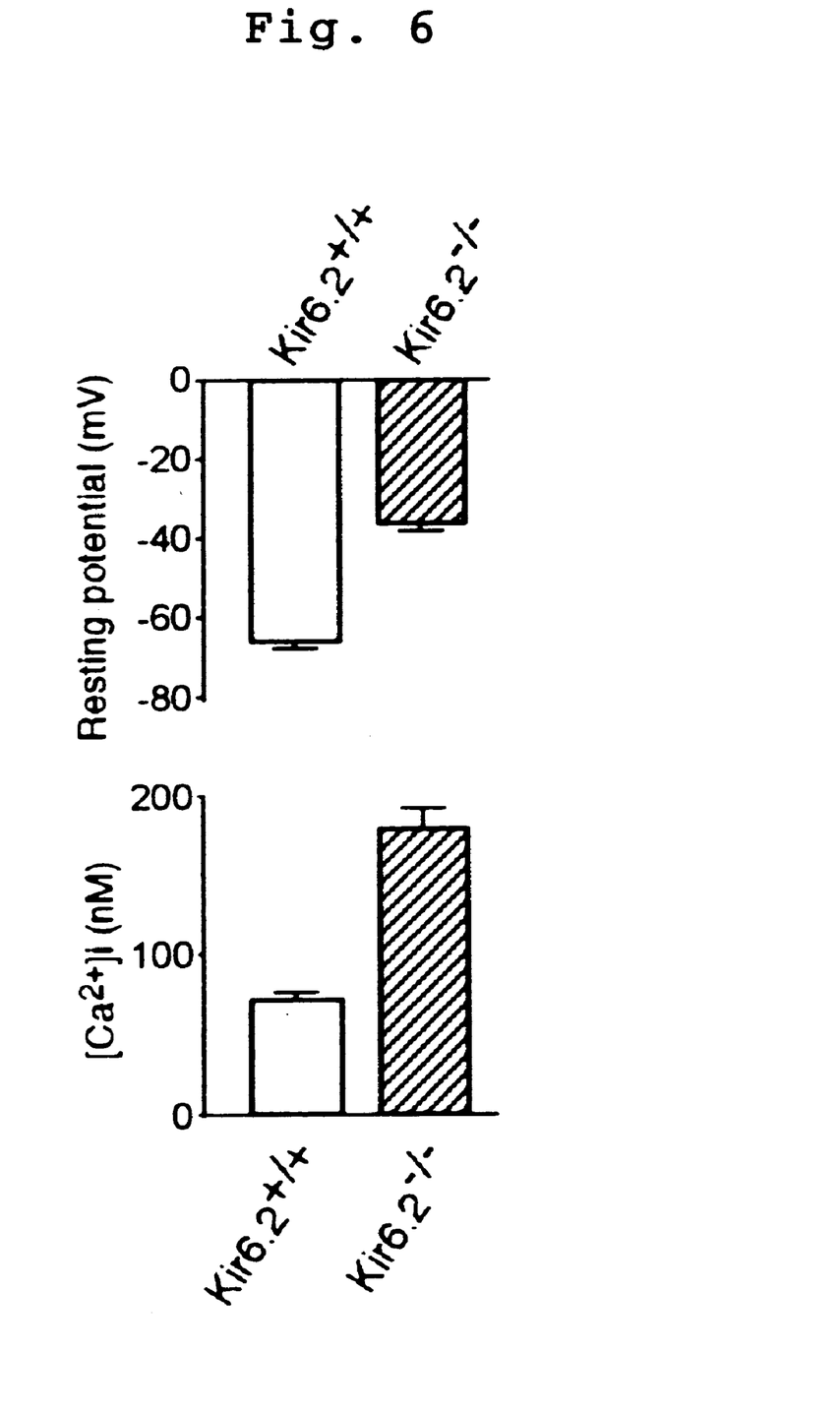
FIG. 6 is a graph showing resting membrane potential and basal intracellular $Ca^{2+}$ concentration, of pancreatic β-cells.

FIG. 6 illustrates resting membrane potential and basal intracellular Ca$^{2+}$ concentration ([Ca$^{2+}$]i) of Kir6.2$^{+/+}$ pancreatic β-cells and Kir6.2$^{-/-}$ pancreatic β-cells. Resting membrane potential was significantly higher in Kir6.2$^{-/-}$ pancreatic β-cells than normal, Kir6.2$^{+/+}$ pancreatic β-cells [Kir6.2$^{-/-}$: −36.1±1.88 mV (n=59); Kir6.2$^{+/+}$: −65.5±1.99 mV (n=59):p<0.001]. In the presence of 2.8 mM glucose, repetitive bursts of action potential were frequently noted (data not shown). At the same glucose concentration, the basal intracellular Ca$^{2+}$ concentration spontaneously fluctuated in Kir6.2$^{-/-}$ pancreatic β-cells, but its mean value was significantly elevated in Kir6.2$^{-/-}$ pancreatic β-cells [Kir6.2$^{-/-}$:179±13.1 nM (n=34); Kir6.2$^{+/+}$:70.9±4.31 nM (n=16): p=<0.001]. In contrast to Kir6.2$^{+/+}$ pancreatic β-cells in which high concentration glucose (16.7 mM) induced depolarization of the membrane, membrane potential of Kir6.2$^{-/-}$ pancreatic β-cells was not altered with 16.7 mM glucose (data not shown). These results show that the resting potential in pancreatic β-cells is determined by the $K_{ATP}$ channels.

Since glucose and tolbutamide cause closure of the K$^{ATP}$ channel in pancreatic β-cells, thereby leading to membrane depolarization and calcium influx, we further examined the changes in intracellular Ca$^{2+}$ concentration in the β-cells in response to stimuli with different secretagogues. The secretagogues applied were glucose (16.7 mM), tolbutamide (100 μM), acetylcholine (100 μM), and K$^+$(30 mM).

Figure 7:
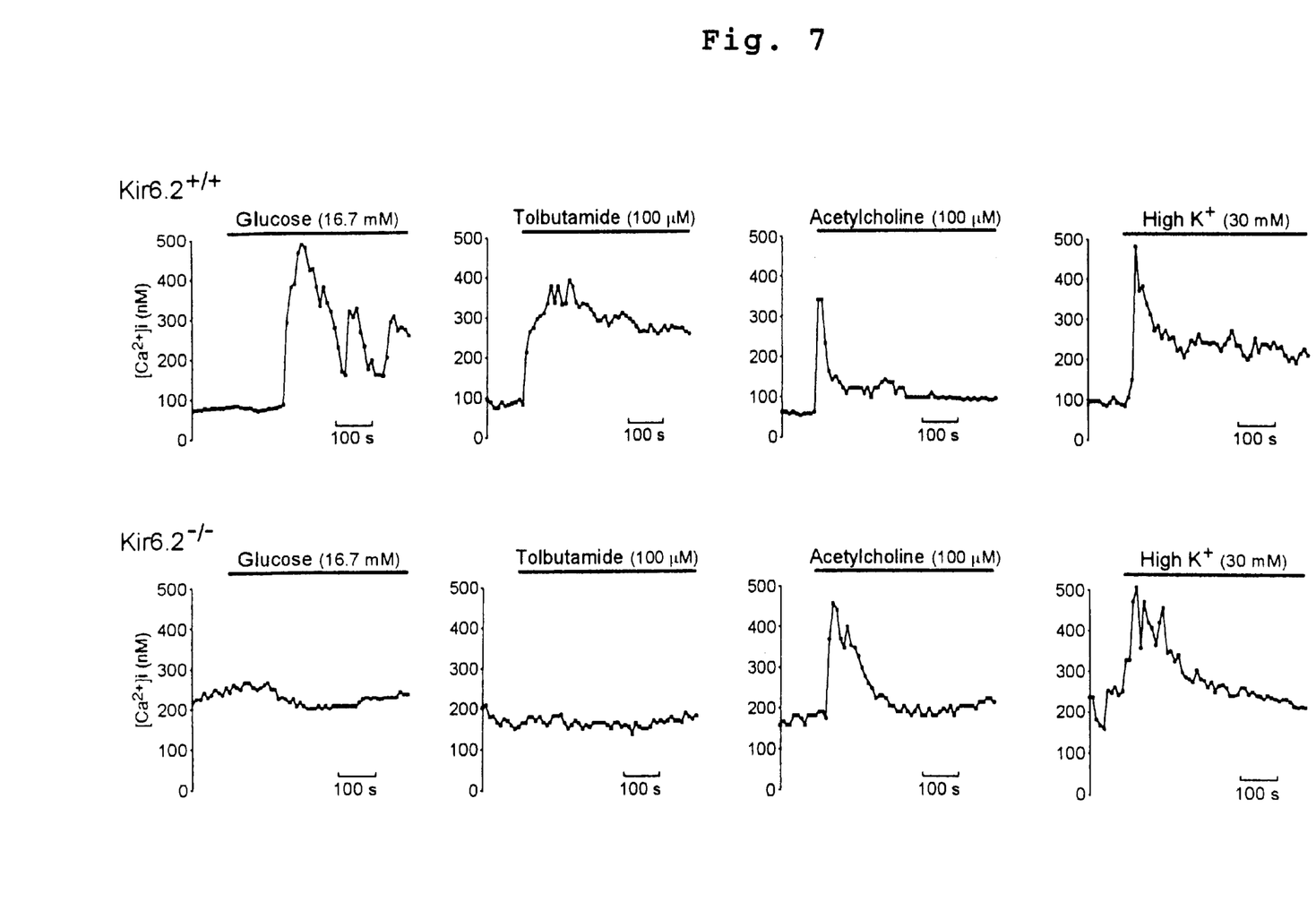
FIG. 7 shows the effect of the secretagogues on intracellular $Ca^{2+}$ concentration in pancreatic β-cells

FIG. 7 illustrates, with reference to typical examples, the effect of these insulin secretagogues on intracellular Ca$^{2+}$ concentration ([Ca$^{2+}$]i) in Kir6.2$^{+/+}$ and Kir6.2$^{-/-}$ pancreatic β-cells, respectively. The horizontal bars in the figure indicate application period of the secretagogues. The figure shows that all of the above secretagogues at their indicated concentrations raised intracellular Ca$^{2+}$ concentrations in Kir6.2$^{+/+}$ pancreatic β-cells and that in Kir6.2$^{-/-}$ pancreatic β-cells, in contrast, while acetylcholine and K$^+$ did raise intracellular Ca$^{2+}$ concentrations to levels comparable to those in Kir6.2$^{+/+}$ pancreatic β-cells, glucose and tolbutamide did not cause any change in intracellular Ca$^{2+}$ concentrations in Kir6.2$^{-/-}$ pancreatic β-cells.

These results confirms that the intracellular calcium mobilization from inositol-1,4,5-triphosphate (IP$_3$)-sensitive Ca$^{2+}$ reservoir and Ca$^{2+}$ influx through voltage-dependent calcium channels are normal in Kir6.2$^{-/-}$ pancreatic β-cells, while indicating that the glucose and tolbutamide-elicited rise of Ca$^{2+}$ in normal pancreatic β-cells requires closure of $K_{ATP}$ channels.

<Insulin Secretory Responses in Batch Incubation>

Insulin secretory responses to glucose and tolbutamide were measured in vitro by batch incubation of pancreatic islets of adult mice.

Batch incubation was performed according to the method of Okamoto et al. [Okamoto, Y. et al., Diabetes 41, 1555–1561 (1992)] with slight modifications. Briefly, pancreatic islets (10 islets in each tube) were preincubated at 37° C. for 60 min in HEPES-Krebs, and then incubated for 30 min in 400 μl of the buffer containing various stimulants of insulin secretion.

Figure 8:
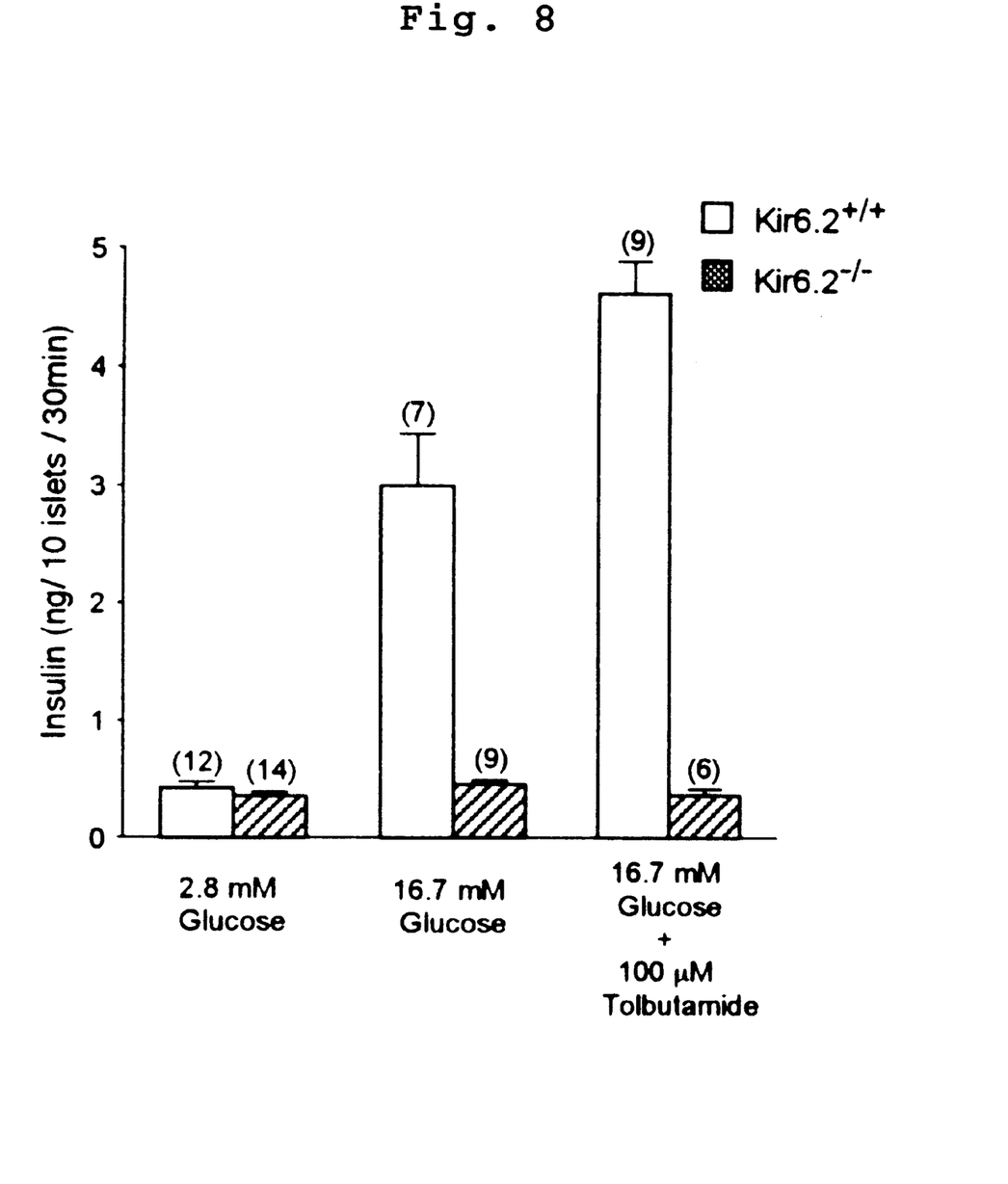
FIG. 8 is a graph showing insulin secretion in batch-incubated pancreatic islets.

FIG. 8 illustrates insulin secretion in batch-incubated Kir6.2$^{+/+}$ and Kir6.2$^{-/-}$ pancreatic islets. Each of the numerals in the brackets above the bars indicates the number of the times of experimentation. Despite the elevated basal levels of intracellular Ca$^{2+}$ in Kir6.2$^{-/-}$ pancreatic β cells, the basal levels of insulin secretion from batch-incubated Kir6.2$^{-/-}$ pancreatic islets were not different from those in Kir6.2$^{+/+}$ cells [Kir6.2$^{+/+}$:0.42±0.05 ng/10 islets/30 min; Kir6.2$^{-/-}$: 0.35±0.04 ng/10 islets/30 min]. In the Kir6.2$^{+/+}$ islets, there was 7.2-fold increase in insulin secretion in response to 16.7 mM glucose, and the secretion was further increased by addition of 100 μM tolbutamide. In the Kir6.2$^{-/-}$ islets, in contrast, 16.7 mM glucose and addition of 100 μM tolbutamide did not cause insulin secretion. In contrast to this, both of 100 μM acetylcholine and 60 mM K$^+$ elicited insulin secretion (data not shown).

These results indicate that a rapid rise in intracellular Ca$^{2+}$ concentration, rather than a sustained elevation, is important for either of the glucose-induced and tolbutamide-induced insulin secretion.

<Insulin Secretory Responses in Perfusion Experiment>

Next, insulin secretory responses to glucose and tolbutamide were determined in vitro by means of perfusion of pancreatic islets of adult mice.

Perfusion of pancreatic islets were performed according to the method of Wollheim et al.[Wollheim, C, et al., in Methods in Enzymology, eds. Fleischer, S. & Fleischer B., (Academic Press Inc., San Diego), vol.192, p.188–223 (1990)]. Briefly, 150 islets were placed in a column with Bio-Gel P-2 (Bio-Rad, California, USA), and continuously perfused with gassed HEPES-Krebs buffer containing 118.4 mM NaCl, 4.7 mM KCl, 1.2 mM KH$_2$PO$_4$, 2.4 mM CaCl$_2$, 1.2 mM MgSO$_4$, 20 mM NaHCO$_3$, 2.8 mM glucose, and 10 mM HEPES, supplemented with 0.2% (w/v) bovine serum albumin, at a constant flow rate of 0.5 ml/min at 37° C. After preincubation for 60 min, different stimulants of insulin secretion were applied.

Figure 9:
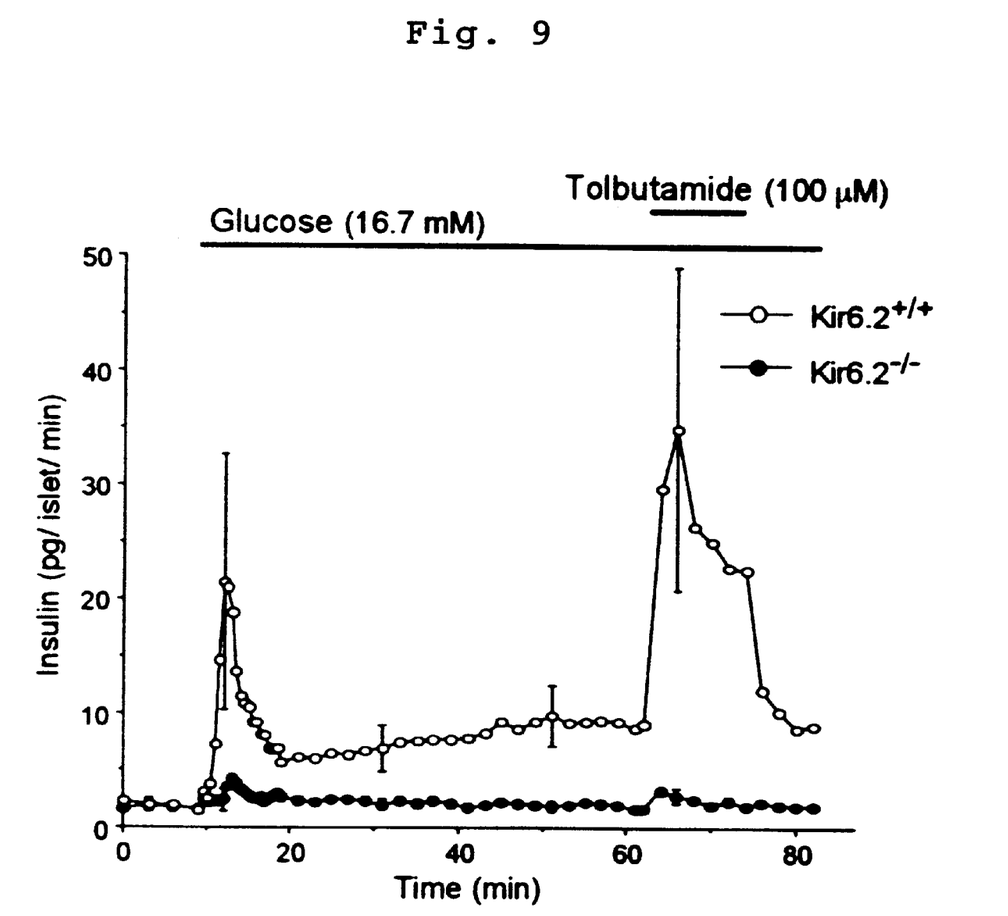
FIG. 9 is a graph showing the time course of insulin secretory responses to glucose and tolbutamide in perfused pancreatic islets.

FIG. 9 illustrates the time course of insulin secretory responses to glucose and tolbutamide in perfused Kir6.2$^{+/+}$ and Kir6.2$^{-/-}$ pancreatic islets. For each experiment, pancreatic islets were isolated from 3–5 Kir6.2$^{+/+}$ and Kir6.2$^{-/-}$ animals, respectively. The mean value and SE were obtained from 4 and 5 experiments for Kir6.2$^{+/+}$ and Kir6.2$^{-/-}$ animals, respectively. The horizontal bars indicate application periods of the agents. There was no significant difference in the basal levels of insulin secretion in the presence of 2.8 mM glucose [Kir6.2$^{+/+}$:2.04±0.50 pg/islet/min; Kir6.2$^{-/-}$:1.92±0.41 pg/islet/min]. In perfusion of Kir6.2$^{-/-}$ pancreatic islets, only a trace amount of insulin secretion was detected in the first phase in response to 16.7 mM glucose, and no secretion was observed in the second phase. 100 μM tolbutamide in the presence of 16.7 mM glucose did not stimulate insulin secretion in Kir6.2$^{-/-}$. That the 6.2$^{-/-}$ pancreatic islets exhibited only a very limited insulin response in vivo to glucose indicates that the K$_{ATP}$ channels are critical in both of the first and second phases of glucose-induced insulin secretion.

<Glucose Tolerance Test>

Glucose (1 g/kg) was injected intraperitoneally into anesthetized mice (10–16 weeks) after fasting for 16 hours, and blood glucose levels and serum insulin concentrations were followed.

Figure 10:
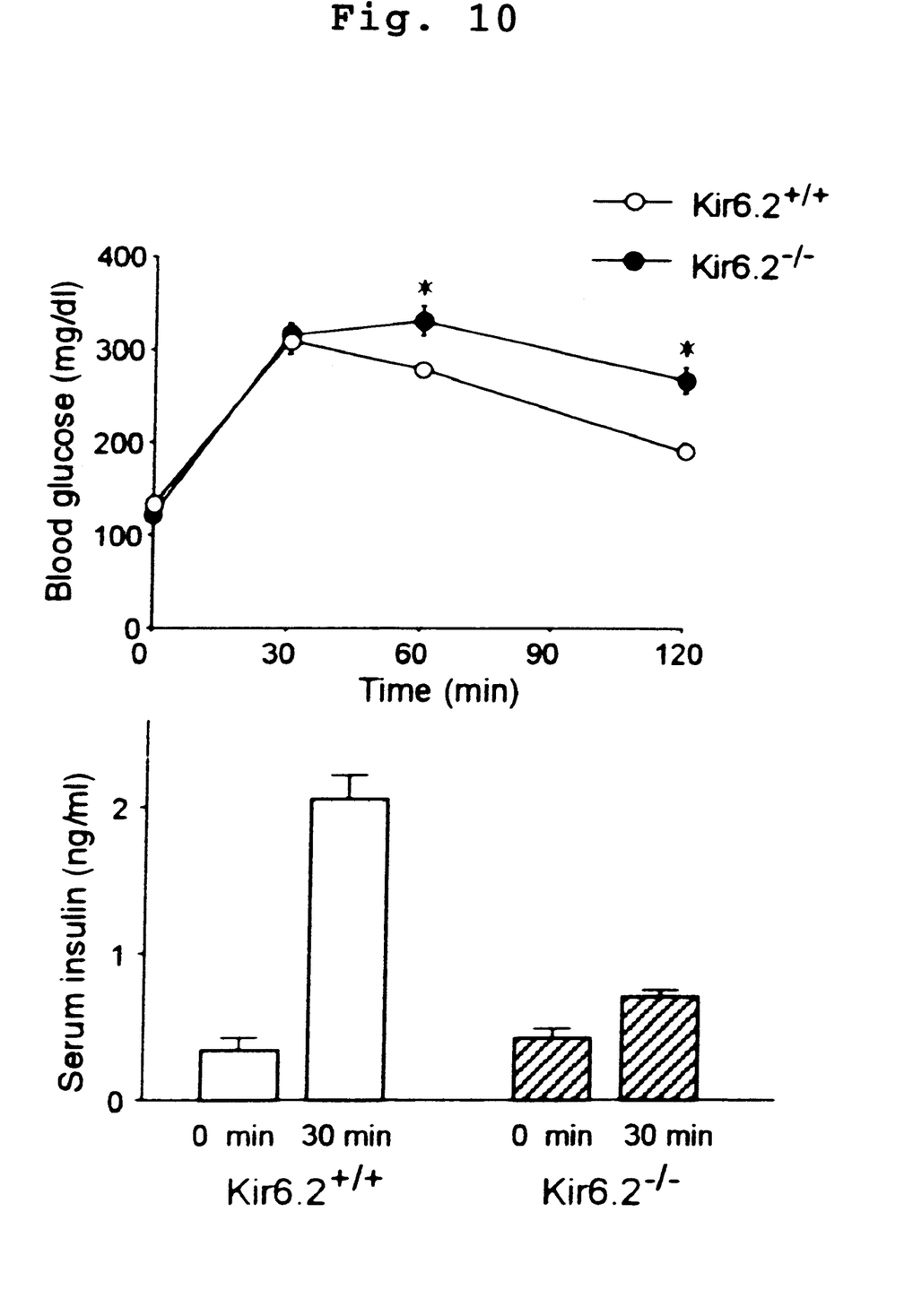
FIG. 10 is a graph showing the response to glucose loading in blood glucose levels and serum insulin concentrations.

FIG. 10 illustrates the results of the glucose tolerance test. The upper graph shows the change in blood glucose levels and the lower graph the change in serum insulin concentrations, respectively. Fasting blood glucose levels were 132±6 mg/dl for Kir6.2$^{+/+}$ (n=11) and 121±8 mg/dl for Kir6.2$^{-/-(n=11)}$. The blood glucose levels 60 and 120 min after glucose load were slightly higher in Kir6.2$^{-/-}$ than Kir6.2$^{+/+}$[332±16 mg/dl and 279±8 mg/dl, respectively, (60 min) (n=11): 268±14mg/dl and 192±8 mg/dl, respectively, (120 min) (n=11): p<0.01]. Serum insulin concentrations, compared between before and after glucose loading, showed changes from 0.34±0.09 ng/ml to 2.05±0.17 ng/ml for Kir6.2$^{+/+}$ (n=6; p<0.001), and from 0.42±0.07 ng/ml to 0.70±0.05 ng/ml for Kir6.2$^{-/-}$ (n=6; p<0.01).

Thus, unexpectedly, despite the defect in glucose-induced insulin secretion, glucose tolerance was found to be impaired only slightly in Kir6.2$^{-/-}$ mice. In addition, blood glucose levels at random measurements in Kir6.2$^{-/-}$ mice (12 weeks) were not different from those in age-matched normal mice [Kir6.2$^{-/-}$:191±6.4 mg/dl (n=33): Kir6.2$^{+/+}$: 188±3.8 mg/dl (n=29)].

<Insulin Loading Test>

Figure 11:
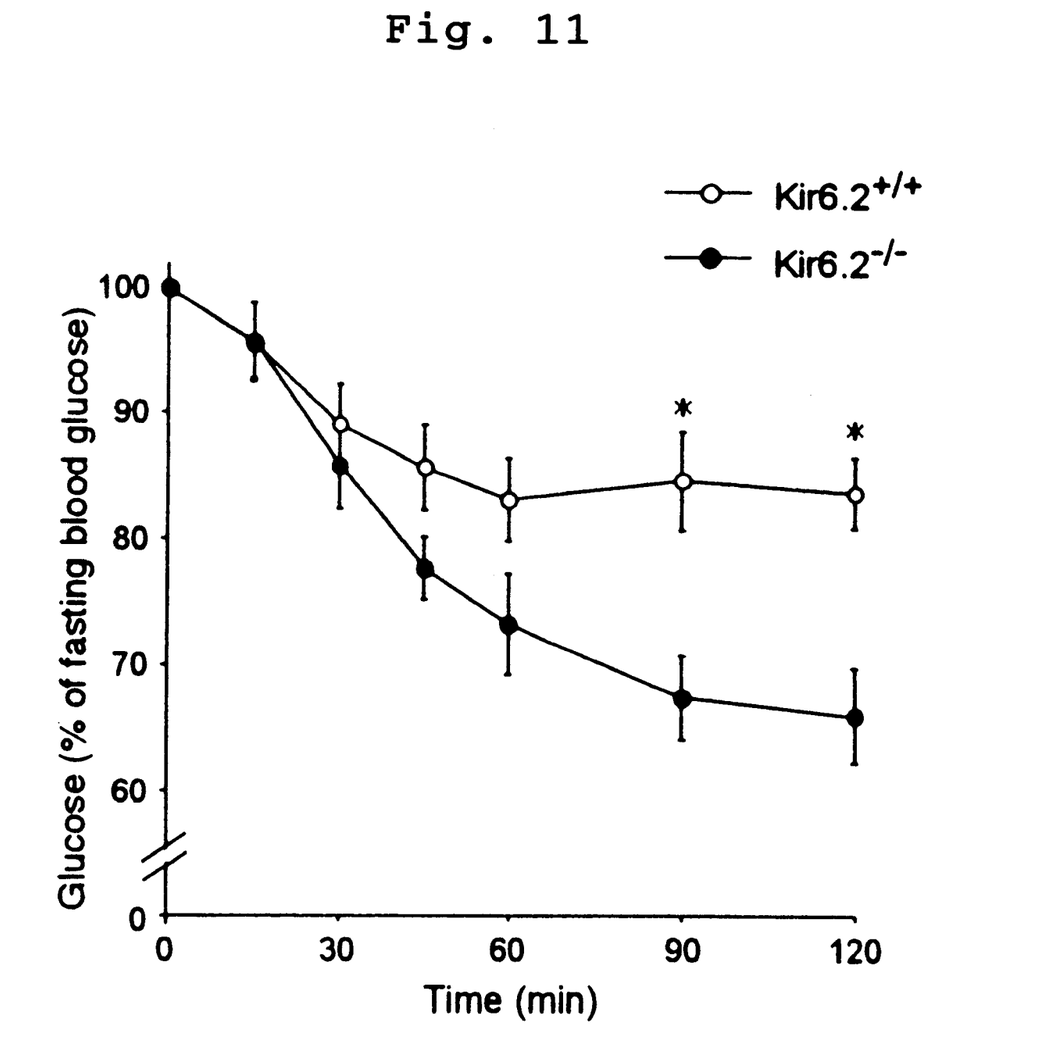
FIG. 11 is a graph showing the results of insulin loading test.

Since an enhanced glucose lowering effect of insulin would account for these results in Kir6.2$^{-/-}$ mice, we, in order to check the hypothesis, injected them with a relatively low dose of insulin (0.1 U/kg) and examined changes in blood glucose levels. FIG. 11 illustrates the results of insulin loading test. Insulin (0.1 U/kg) was injected intraperitoneally in anesthetized adult mice (10–16 weeks) after fasting for 16 hours. The blood glucose levels 90 and 120 min after glucose loading were significantly lower in Kir6.2$^{-/-}$ than those in Kir6.2$^{+/+}$ [67.4±3.4% for Kir6.2$^{-/-}$ vs 84.7±3.9% for Kir6.2$^{+/+}$(90 min); 66.0±3.8 for Kir6.2$^{-/-}$ vs 83.7±2.8% for Kir6.2$^{+/+}$(120 min): *p<0.01]. As shown by the results, the glucose-lowering effect of insulin was significantly increased in Kir6.2$^{-/-}$ mice compared with Kir6.2$^{+/+}$ mice.

Whether or not glucose-induced and sulfonylurea-induced insulin secretion are dependent on K$_{ATP}$ channels remains controversial [Cook, D. L. et al., Diabetes, 37:495–498 (1988); Takasawa, S. et al., Science, 259:370–373 (1993); Gembal, M. et al., J. Clin. Invest., 91:871–880 (1993); Komatsu, M. et al., Proc. Natl. Acad. Sci. USA, 92: 10728–10732 (1995); Eliasson, L. et al., Science, 271:812–815 (1996)]. As shown, it has been found that glucose at high concentrations does not stimulate insulin secretion in Kir6.2$^{-/-}$, and that tolbutamide, even in the presence of high concentrations of glucose, does not elicit insulin secretion, suggesting strongly that glucose metabolism itself is not sufficient for either glucose-induced or tolbutamide-induced insulin secretion. The above results demonstrate that both glucose-induced and sulfonylurea-induced insulin secretion require the rapid rise in intracellular Ca$^{2+}$ concentration caused by closure of the K$_{APT}$ channels.

The present study shows that disruption of K$_{ATP}$ channels increases insulin-induced glucose disposal in vivo. Interestingly, in addition to stimulating insulin secretion, sulfonylureas have been shown to potentiate insulin-stimulated glucose transport in skeletal muscle [Simpson, I. A. et al., Ann. Rev. Biochem., 55:1059–1089 (1986)], the major site of glucose disposal [Wang, P. H. et al., J. Clin. Invest, 84:62–67 (1989); Pulido N. et al., Diabetologia, 39:22–27 (1996)], supporting also that the skeletal muscle K$_{ATP}$ channel modulates insulin-stimulated glucose transport.

Mutation in SUR1 or Kir6.2 in human could cause persistent hyperinsulinemic hypoglycemia of infancy (PHHI), a disorder characterized by unregulated insulin secretion [Thomas, P. M. et al., Science, 268:426–429 (1995); Kane, C. et al., Nature Med., 2:1344–1347 (1996); Nichols, C. G. et al., Science, 272:1785–1787 (1996); Dunne, M. I. et al., N. Engl. J. Med., 336:703–706 (1997); Nestorowicz, A. et al., Diabetes, 46:1743–1748 (1007)], and our data shows a transient hypoglycemia in neonatal Kir6.2$^{-/-}$ animals. Since SUR1 is a subunit specific to the β-cell K$_{ATP}$ channel and Kir6.2 is a subunit of both the β-cell and skeletal muscle K$_{ATP}$ channels, the consequences of mutations in SUR1 and Kir6.2 could differ in terms of insulin action.

As aformentioned, the K$_{ATP}$ channels in pancreaticβ-cells is essential for glucose-induced and sulfonylurea-induced insulin secretion. In addition, the K$_{ATP}$ channels in skeletal muscle modulates insulin action, by a mechanism which remains to be elucidated.

What is claimed is:

1. A transgenic mouse homozygous for a disruption in the Kir6.2 gene, whereby no functional Kir6.2 is produced, and wherein pancreatic β-cells and skeletal muscle cells of the mouse have complete loss of $K_{ATP}$ channel activity.

2. A tissue of the mouse of claim 1 selected from the group consisting of pancreatic tissue, skeletal muscular tissue, myocardial tissue, pituitary gland tissue and vascular endothelial tissue.

3. A cell of the mouse of claim 1 selected from the group consisting of a Langerhans' β-cell, a skeletal muscular cell, a myocardial cell, a pituitary gland cell, and a vascular endothelial cell.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH:1173 base pairs
       (B) TYPE:nucleic acid
       (C) STRANDEDNESS:double
       (D) TOPOLOGY:linear (ii) MOLECULE TYPE:genomic DNA (iii) HYPOTHETICAL:no (iv) ANTI-SENSE:no (xi) SEQUENCE DESCRIPTION:SEQ ID NO:1:

```
ATGCTGTCCC GAAAGGGCAT TATCCCTGAG GAATATGTGC TGACCCGGCT GGCAGAGGAC      60
CCTGCAGAGC CCAGGTACCG TACTCGAGAG AGGAGGGCCC GCTTCGTGTC CAAGAAAGGC     120
AACTGCAACG TCGCCCACAA GAACATTCGA GAGCAGGGCC GCTTCCTGCA GGATGTGTTC     180
ACCACGCTGG TGGACCTCAA ATGGCCACAC ACTCTGCTCA TTTTCACCAT GTCCTTCCTG     240
TGCAGCTGGC TGCTCTTTGC CATGGTCTGG TGGCTCATCG CCTTCGCCCA CGGTGACCTG     300
GCCCCCGGAG AGGGCACCAA TGTGCCCTGC GTCACAAGCA TCCACTCCTT TTCATCTGCC     360
TTCCTTTTCT CCATCGAGGT CCAGGTGACC ATTGGTTTCG GCGGGCGCAT GGTGACAGAG     420
GAATGTCCCC TGGCCATCCT CATTCTCATT GTGCAGAATA TCGTCGGGCT GATGATCAAC     480
GCCATCATGC TGGGCTGCAT CTTCATGAAA ACGGCCCAGG CCCATCGGCG GGCAGAAACC     540
CTCATCTTCA GCAAGCATGC TGTGATCACC CTGCGCCATG GCCGCCTGTG CTTCATGCTG     600
CGCGTAGGGG ACCTCCGAAA GAGCATGATC ATTAGCGCCA CCATCCACAT GCAGGTGGTG     660
CGCAAGACCA CCAGCCCCGA GGGCGAAGTT GTGCCTCTCC ACCAGGTAGA CATCCCCATG     720
GAGAATGGCG TGGGTGGTAA CGGCATCTTC CTGGTGGCCC CACTCATCAT CTACCACGTC     780
ATCGACTCCA ACAGCCCGCT CTACGACCTG GCTCCTAGTG ACCTGCACCA CCACCAGGAC     840
CTGGAGATCA TTGTCATCTT GGAAGGCGTG GTAGAAACCA CGGGCATCAC CACCCAGGCC     900
CGCACCTCCT ACCTAGCTGA CGAGATTCTA TGGGGGCAGC GCTTTGTCCC CATTGTGGCC     960
GAGGAGGACG GCCGCTATTC TGTGGACTAC TCCAAATTTG GTAACACCAT TAAAGTGCCC    1020
ACACCACTCT GCACAGCCCG CCAGCTTGAT GAGGACCGCA GTCTGCTGGA TGCCCTGACC    1080
CTCGCCTCGT CGCGGGGGCC CCTGCGCAAG CGCAGTGTGG CTGTGGCGAA GGCCAAGCCC    1140
AAGTTTAGCA TCTCTCCAGA TTCCTTGTCC TGA                                  1173
```